(12) United States Patent
Korkala et al.

(10) Patent No.: US 10,070,798 B2
(45) Date of Patent: Sep. 11, 2018

(54) HEART ACTIVITY SENSOR STRUCTURE

(71) Applicant: Polar Electro Oy, Kempele (FI)

(72) Inventors: Seppo Korkala, Kempele (FI); Elias Pekonen, Oulu (FI); Juhani Kemppainen, Oulu (FI); Pekka Rytky, Oulu (FI)

(73) Assignee: Polar Electro Oy, Kempele (FI)

( * ) Notice: Subject to any disclaimer, the term of this patent is extended or adjusted under 35 U.S.C. 154(b) by 101 days.

(21) Appl. No.: 14/274,137

(22) Filed: May 9, 2014

(65) Prior Publication Data
US 2014/0343391 A1 Nov. 20, 2014

(30) Foreign Application Priority Data
May 15, 2013 (EP) ..................................... 13167788

(51) Int. Cl.
| | | |
|---|---|---|
| *A61B 5/04* | (2006.01) | |
| *A61B 5/0408* | (2006.01) | |
| *A61B 5/0245* | (2006.01) | |
| *A61B 5/00* | (2006.01) | |

(52) U.S. Cl.
CPC .......... *A61B 5/0408* (2013.01); *A61B 5/0245* (2013.01); *A61B 5/04085* (2013.01); *A61B 5/6804* (2013.01); *A61B 5/6823* (2013.01); *A61B 5/6831* (2013.01); *A61B 2562/164* (2013.01); *A61B 2562/182* (2013.01); *Y10T 29/4913* (2015.01)

(58) Field of Classification Search
CPC ... A61B 5/0006; A61B 5/6831; A61B 5/0402; A61B 5/0478; A61B 5/0245; A61B 5/7203; A61B 2562/182; A61N 1/0492; A61N 1/0484

USPC ................ 600/372, 382, 384, 386, 388–393, 600/508–509
See application file for complete search history.

(56) References Cited

U.S. PATENT DOCUMENTS 3,534,727 A * 10/1970 Roman .............. A61B 5/04085
                                                    600/389
4,122,843 A * 10/1978 Zdrojkowski ........ A61B 5/6831
                                                    600/382
4,763,660 A *  8/1988 Kroll .................. A61B 5/04085
                                                    439/77

(Continued)

FOREIGN PATENT DOCUMENTS

| EP | 2057943 A1 | 5/2009 |
|---|---|---|
| GB | 2438953 A | 12/2007 |
| WO | 2012/104484 A1 | 8/2012 |

OTHER PUBLICATIONS

European Search Report, Application No. EP 13 16 7788, dated Nov. 21, 2013, 2 pages.

*Primary Examiner* — Joseph Stoklosa
*Assistant Examiner* — Brian M Antiskay
(74) *Attorney, Agent, or Firm* — FisherBroyles, LLP

(57) ABSTRACT

A heart activity sensor structure includes a flexible textile substrate, and at least two electrodes with an electric insulation between each of the at least two electrodes. The at least two electrodes are applied on one side of the flexible textile substrate and configured to be placed against a skin of an exerciser in order to measure biosignals related to heart activity. The heart activity sensor also includes an electrostatic discharge shield applied on one side of the flexible textile substrate for protecting the at least two electrodes from static electricity.

11 Claims, 5 Drawing Sheets

(56) References Cited

U.S. PATENT DOCUMENTS

| | | | |
|---|---|---|---|
| 5,483,967 A * | 1/1996 | Ohtake | A61B 5/04085 |
| | | | 128/903 |
| 5,491,474 A | 2/1996 | Suni et al. | |
| 5,782,241 A * | 7/1998 | Felblinger | A61B 5/02438 |
| | | | 128/908 |
| 6,327,486 B1 | 12/2001 | Nissila et al. | |
| 6,453,186 B1 | 9/2002 | Lovejoy et al. | |
| 7,680,523 B2 * | 3/2010 | Rytky | A61B 5/0245 |
| | | | 600/372 |
| 8,190,230 B2 * | 5/2012 | Rytky | A61B 5/0408 |
| | | | 174/350 |
| 2010/0160763 A1 | 6/2010 | Tsai et al. | |
| 2013/0178728 A1 * | 7/2013 | Vandermeiden | A61B 5/0245 |
| | | | 600/390 |

\* cited by examiner

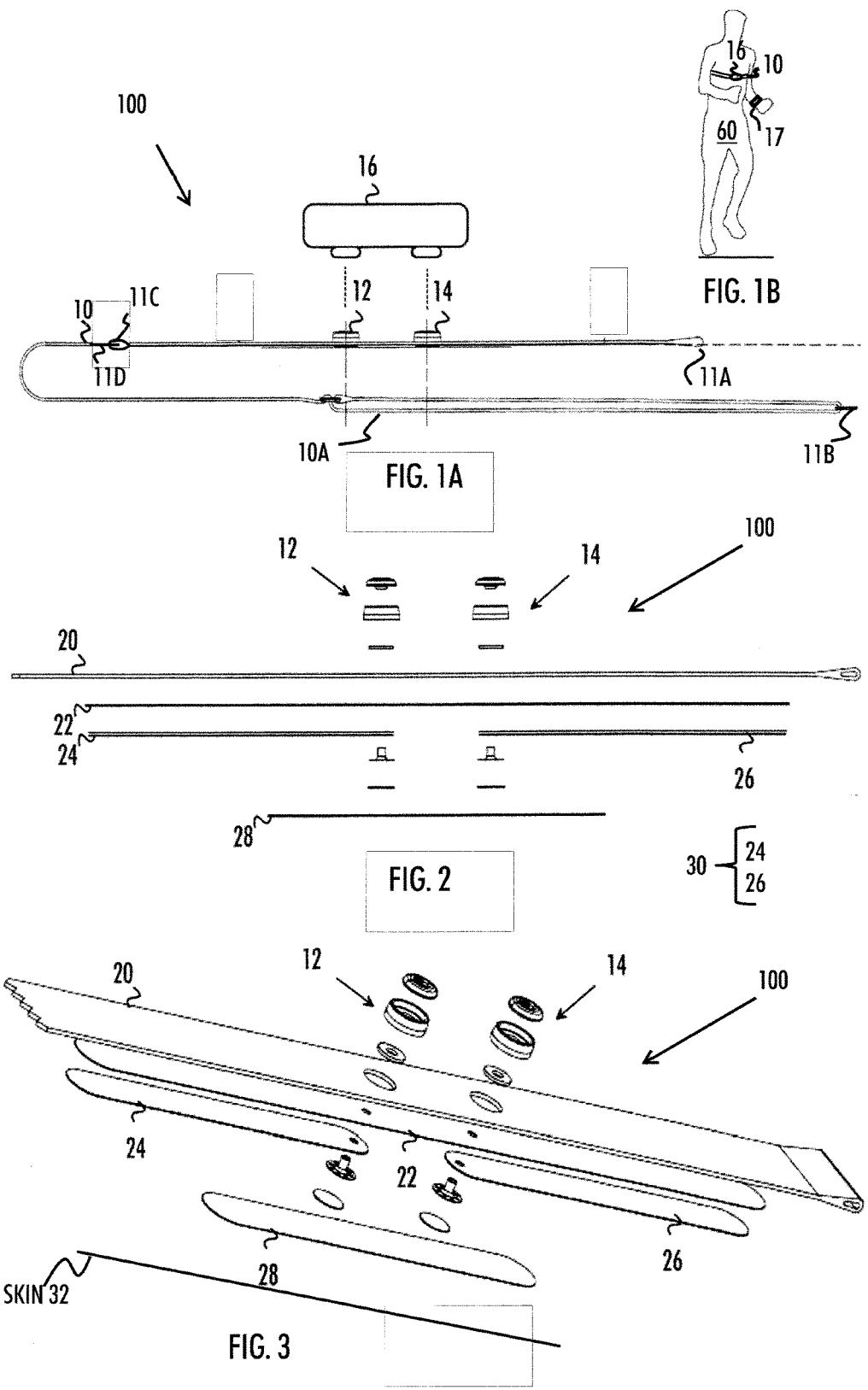

HEART ACTIVITY SENSOR STRUCTURE

CROSS-REFERENCE TO RELATED APPLICATION

This application claims priority to European Patent Application No. 13167788.2, filed May 15, 2013, which is incorporated by reference herein in its entirety.

BACKGROUND

Field The invention relates generally to heart activity sensors. More particularly, the invention relates to a structure of the heart activity sensor used while exercising.

Description of the Related Art

It is common to measure heart activity while exercising in order to better monitor the effect of the exercise by the exerciser. The measuring may comprise, for example, determining the heart rate or the heart rate variation of the exerciser. Typically this is done by wearing a heart rate activity sensor having electrodes against the skin of the exerciser. However, the conditions for measuring the heart activity while exercising are harsh.

SUMMARY

According to an aspect of the invention, there is provided a heart activity sensor structure as specified in claim 1.

According to an aspect of the invention, there is provided a method as specified in claim 15.

Embodiments of the invention are defined in the dependent claims.

BRIEF DESCRIPTION OF THE DRAWINGS

In the following, the invention will be described in greater detail with reference to the embodiments and the accompanying drawings, in which FIGS. 1A, 1B, 2, and 3 present a heart rate sensor structure to which the embodiments are applicable to;

DETAILED DESCRIPTION

Figure 4A:
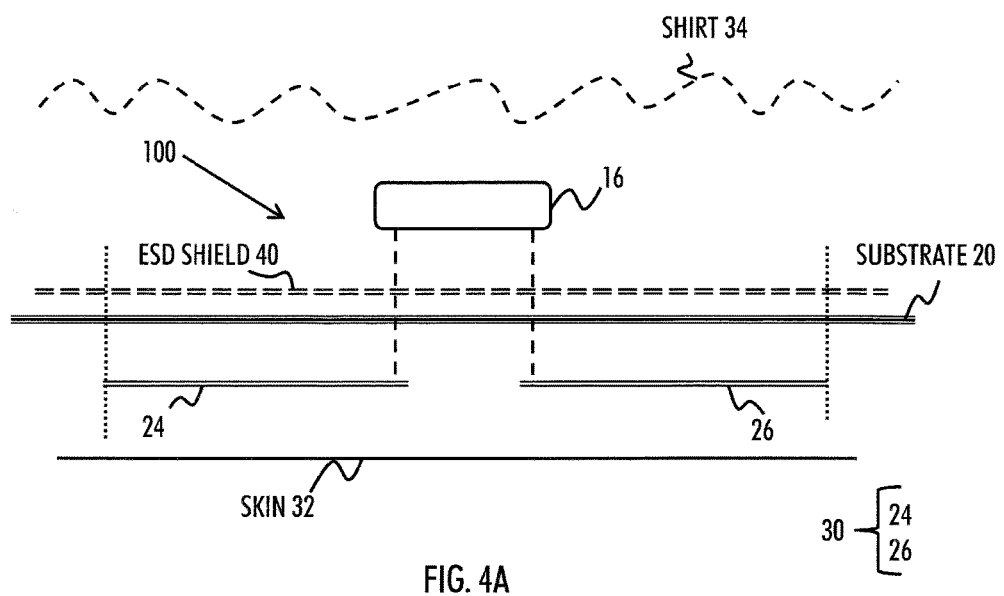
FIGS. 4A and 4B represent an electrostatic discharge (ESD) shield applied to the heart rate sensor structure according to some embodiments.

The following embodiments are exemplary. Although the specification may refer to "an", "one", or "some" embodiment(s) in several locations of the text, this does not necessarily mean that each reference is made to the same embodiment(s), or that a particular feature only applies to a single embodiment. Single features of different embodiments may also be combined to provide other embodiments.

As said, it is common to measure heart activity while exercising in order to better monitor the effect of the exercise by the exerciser. Typically the measuring takes place with a heart rate activity sensor having electrodes against the skin of the exerciser. The location of the skin may be, e.g. the chest of the exerciser. The electrodes may measure voltage variations on the skin wherein the variations are due to the activity of the heart muscle. As a result, an electrocardiogram (ECG) signal may be generated. From the ECG signal, a variety of information may be derived. These include heart rate or heart rate variation, for example.

The voltage changes may be in the range of millivolts, thus making the detection of the changes relatively difficult. Further, the conditions for measuring the heart activity while exercising are harsh due to, e.g., movement of the exerciser. At least partly for this reason, it is known to use a flexible textile as a substrate for mounting the electrodes which are placed against the chest of the exerciser. This is because the flexible textile is comfortable to the user compared to an integrated heart activity sensor structure. Furthermore, a flexible textile adapts better to the body shape of the exerciser and thereby ensures a better electrode contact to skin of the exerciser. An integrated heart activity sensor structure is disclosed in U.S. Pat. Nos. 5,491,474 and 6,327,486 which are hereby incorporated by reference.

The integrated heart activity sensor structure is significantly different than a sensor structure applying the flexible textile in the point of view of the functionality and from the point of view of the implementation and assembly. For example, in the integrated heart activity sensor, electrodes and transmitter electronics are both functional entities molded into a single plastic casing. The plastic casing structure is simple, durable and relatively easy to manufacture. However, the structure is relatively rigid, thus having a negative impact on the user experience. On the contrary, in the sensor structure applying the flexible textile substrate, the electrode structure is typically implemented with conductive plastic or textile applied on an elastic strap.

With reference to an embodiment shown in FIGS. 1A and 1B, let us consider an embodiment of a heart activity sensor structure 100 to which embodiments of the invention may be applied. The heart activity sensor structure 100 may be attached to, e.g., a strap 10, which the exerciser 60 may wear around his/her body, such as chest, in order to hold electrodes, which are comprised in the heart activity sensor structure 100, firmly against the skin 32 during the exercise. The exerciser 60 is the user of the heart activity sensor structure 100. The heart activity sensor structure 100 may comprise fastening elements 11A and 110 for detachably fastening/connecting the heart activity sensor structure 100 to fastening elements 11 B and 11 D of the strap 10, respectively. The strap 10 may comprise a length adjustment portion 10A adjusting the length of the strap by the exerciser 60. In an embodiment, the heart activity sensor structure 100 comprises the strap 10. It should be noted that the heart activity sensor structure 100 may alternatively be attached to a garment, such as a shirt, a top, a bra, a wristband or trousers, instead of the strap 10. In an embodiment, the garment is a glove, sock, a shirt arm, or a trouser leg.

The heart activity sensor structure 100 may comprise one or more skin electrodes used to receive a physiological signal from the skin of the user 60, and an electronic circuit may be used to process and measure the physiological signal. The electronic circuit may be installed to an electronics module 16 which may be fixed or detachably attached to the strap 10 through instant connectors 12, 14, such as press stud connectors. The electronics module 16 may further comprise a battery for powering the heart activity sensor structure 100, wherein the battery may be rechargeable or disposable.

The electronics module 16 may also comprise a wireless transmitter circuitry. Then, the measuring device may realize exercise data transmission to a training computer 17, such as to a wrist watch or to a portable receiver, e.g. a mobile phone. In an embodiment, the data transmission carries exercise data to the training computer 17. In an embodiment, the transmitted signal may carry, for instance, ECG information. In an embodiment, the electronics module 16 may be configured to measure, for instance, a physiological signal such as an electromyogram (EMG) from the skin of the user 60. In an embodiment, the heart activity sensor structure 100 may also comprise a receiver for reception of data wirelessly from another device, such as from the training computer 17. In an embodiment, the received data may comprise information needed for upholding the communication connection and/or information needed for reconfiguring the electronics module 16. Thus, the communication link to/from the electronic module 16 may, in an embodiment, be bi-directional.

Let us now consider the structure of the heart activity sensor structure 100 in greater detail with reference to an embodiment illustrated in FIGS. 2 and 3. FIGS. 2 and 3 illustrate different explosion views of the components of the heart activity sensor structure 100, wherein FIG. 2 is a side view, and FIG. 3 is a perspective view. Referring to FIGS. 2 and 3, the heart activity sensor structure 100 comprises the flexible textile substrate 20, also known as a base layer or a supporting layer. The flexible textile substrate 20 may form the base of the heart activity sensor structure 100, and the flexible textile substrate 20 may comprise textile that supports the heart activity sensor structure 100. The flexible textile substrate 20 may comprise woven or knitted textile with elastic components, such as rubber and/or thermoplastic. The flexible textile substrate 20 may form a substrate for mounting at least the electrodes 24, 26. The physical dimensions of the flexible textile substrate 20 may be in the order of 15 cm times 2 cm (length x width).

In an embodiment, the flexible textile substrate 20 is bendably flexible (e.g. flexible so that the textile substrate 20 may be bent, flexed or twisted without breaking). In an embodiment, the flexible textile substrate 20 is stretchably flexible (e.g. flexible so that it may be stretched in longitudinal and/or transversal direction).

The heart activity sensor structure may further comprise an electrode layer 30 comprising one or more electrodes 24, 26. The at least two electrodes 24, 26 may be applied on one side of the flexible textile substrate 20 and configured to be placed against (contact) the skin 32 of the exerciser 60 either directly or indirectly. The electrodes 24, 26 may measure biosignals related to heart activity, such as ECG signals, from the skin 32 of the exerciser 60 and convey the detected electric signals to the electronics module 16 connected to the connectors 12, 14. The electrodes 24, 26 may be made at least partially of a conductive material, e.g. conductive silicon, conductive thermoplastic and/or conductive yarn. The connectors 12, 14 may be disposed to penetrate the flexible textile substrate 20 and any layer between the flexible textile substrate 20 and the electrode layer 30 to provide a galvanic connection between the electrodes 24, 26 and the electronics module 16 disposed on opposite sides of the flexible textile substrate 20. In the embodiment shown in FIGS. 2 and 3, the connectors 12, 14 penetrate also the electrode layer 30, e.g. each electrode 24, 26.

An intermediate insulation layer 22 may be provided as an intermediate layer between the flexible textile substrate 20 and the electrode layer 30. The intermediate insulation layer 22 functions as an electric insulation layer insulating the electrode layer 30 from the flexible textile substrate 20. However in an embodiment, there is no need for the intermediate insulation layer 22 in case the flexible textile substrate 20 is not electrically conductive or is not directly contacting the electrodes. It should be noted though that the flexible textile substrate 20 may become electrically conducting after absorbing moisture during the exercise.

The definition of the electrode layer 30 should be interpreted broadly to cover an electrode layer comprising at least two skin electrodes 24, 26 which may be electrically isolated from each other. In an embodiment, one of the at least two skin electrodes 24, 26 may be coupled to a ground, and a physiological signal delivered by at least one other skin electrode may be amplified and measured with respect to the ground. Alternatively, a difference signal detected between the skin electrodes 24, 26 may be amplified and measured with respect to the ground. The ground level may be defined by a skin 32 or a user's body part, such as chest or arm. The electrodes module 16 may comprise a differential amplifier to perform the amplifying of the difference signal.

When the number of electrodes 24, 26 is higher than one, the electrodes 24, 26 may be electrically isolated/insulated from each other. The electrical isolation from a surface contacting the skin 32 of the exerciser 60 may be achieved by providing a skin insulation layer 28 such that the electrodes 24, 26 are at least partially disposed between the skin isolation layer 28 and the flexible textile substrate 20. The skin isolation layer 28 reduces a short circuit between the electrodes 24, 26 through the skin 32 of the exerciser 60. The skin insulation layer 28 comprises insulating material, such as thermoplastic material, to carry out the isolation. In the case the number of electrodes 24, 26 is higher than two, the skin insulation layer 28 may in some embodiments comprise a plurality of separate insulating portions to insulate the different electrodes 24, 26 from each other.

Figure 4B:
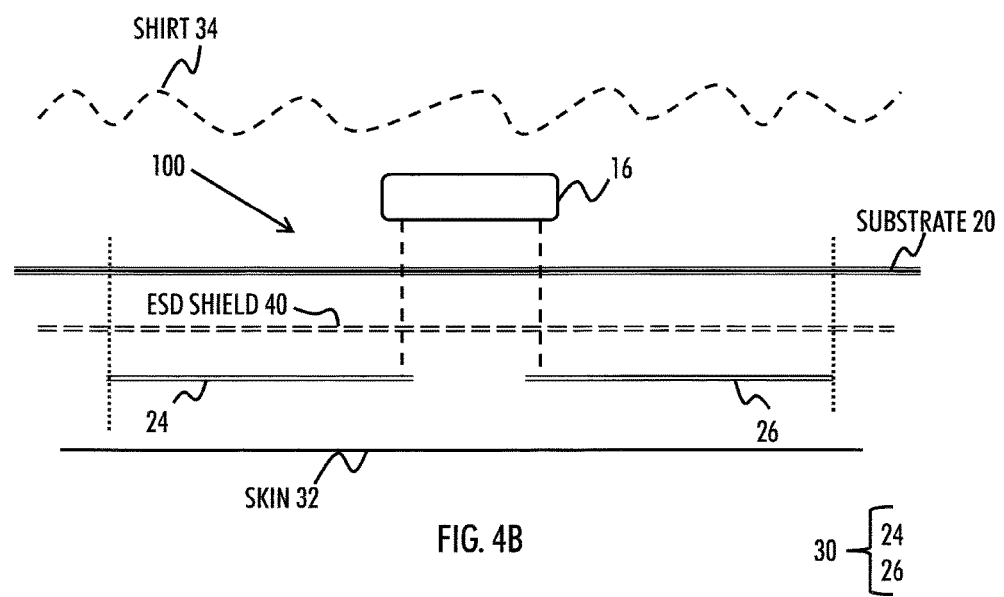

As said earlier, the environmental conditions affect the success of the heart activity measurement, which may be based on detecting millivolt-range signals on the skin 32 of the person 60. These environmental conditions may include static electricity and voltage generation from external sources, such as from the clothes or textiles of the exerciser 60. Accordingly, the heart activity sensor structure 100, as shown in FIGS. 4A and 4B, further comprises an electrostatic discharge (ESD) shield 40 applied on one side of the textile substrate 20 for protecting the at least two electrodes 24, 26 from static electricity. The intermediate insulation layer 22, the skin insulation layer 28, the instant connectors 12, 14, and other through-hole related elements shown in FIGS. 1 to 3 are not depicted in all of the Figures for reasons of simplicity. However, in an embodiment, at least some or all of the omitted elements are comprised in the various embodiments of the heart activity sensor structure 100.

Static electricity may be seen as a contrary to current electricity, which flows via wires or other conductors and transmits energy. The phenomenon of static electricity may be caused whenever two surfaces contact and separate. When two materials are in contact, electrons may move from one material to the other, which leaves an excess of positive charge on one material, and an equal negative charge on the other. When the materials are separated they retain this charge imbalance. In the field of exercising, such two surfaces may be the shirt 34 worn by the exerciser 60 and the heart activity sensor structure 100. The ESD, on other hand, denotes a sudden flow of electricity between two objects, such as the shirt 34 worn by the exerciser 60 and the heart activity sensor structure 100, and may be caused by the static electricity. The ESD may damage the heart activity sensor structure 100 or the ESD may affect the accuracy of the heart activity measurement. However, advantageously due to the application of the ESD shield 40, the possibly generated static electric charges may be conducted away from the vicinity of the electrodes 24, 26, or at least the electric charges may be spread evenly in the vicinity of the electrodes 24, 26. Such even distribution of the static electricity may be beneficial as then the skin electrodes 24, 26 have the same ambient environment and may thus detect the voltage differences on the skin 32 more accurately without being interrupted by the static electricity possibly generated on the opposite side of the electrodes 24, 26 than the skin 32.

In an embodiment, the ESD shield 40 is flexible. In an embodiment, the material of the flexible ESD shield 40 may be any conductive material, such as any metal, e.g. silver or copper. In an embodiment, the ESD shield 40 may be made of a conductive metal tape, metal film or a conductive textile arranged on the opposite side of the electrodes 24, 26 than the skin 32. Thus, the ESD shield 40 may be on the opposite side of the at least two electrodes 24, 26 than the skin 32.

The flexible ESD shield 40 may be applied on (attached to) the flexible textile substrate 20 and, more particularly, on either side of the flexible textile substrate 20. In an embodiment, the ESD shield 40 is arranged on either surface of the flexible substrate 20. Let us look at these closer with reference to FIGS. 4A and 4B. In FIG. 4A, the heart activity sensor 100 comprises at least the following plurality of layers: a first layer comprising the at least two electrodes 24, 26 and configured to be placed against the skin 32 of the exerciser 60, a second layer arranged on top of the first layer and comprising the textile substrate 20, and a third layer arranged at least partially on top of the second layer and comprising the ESD shield 40. Thus, the electrodes 24, 26, the flexible substrate 20 and the flexible ESD shield 40 form layers which may be attached on top of each other. The attachment may be obtained with tape, wire, glue, stitching, knitting, weaving, for example, to mention only a few non-limiting options. The embodiment of FIG. 4A provides ease of implementation as the attachment between the electrodes 24, 26 and the substrate 20 remains as usual. In FIG. 4B, the order of the second and third layers is switched.

In an embodiment, as shown in FIGS. 4A and 4B, the ESD shield 40 covers at least the area in which the at least two electrodes 24, 26 are located. The area in which the at least two electrodes 24, 26 are located may be defined both in length and in width of the heart activity sensor structure 100. From FIGS. 4A and 4B it may be seen that the ESD shield 40 is longer than the area in which the at least two electrodes 24, 26 are located. This is shown by the ESD shield 40 exceeding vertical dotted lines in FIGS. 4A, 4B. The length may be defined in the horizontal dimension on the surface of the skin 32 when the heart activity sensor structure 100 is worn against the chest of the exerciser 60, for example. Further, for example, in FIG. 5B it may be seen that the ESD shield 40 is wider than the area in which the at least two electrodes 24, 26 are located, as shown by the ESD shield 40 exceeding vertical dotted lines in FIG. 5B. The width may be defined in the vertical dimension on the surface of the skin 32 when the heart activity sensor structure 100 is worn against the chest of the exerciser 60, for example. In this way the ESD shield 40 may protect and cover the electrodes 24, 26 from the static electricity efficiently.

Figure 5A:
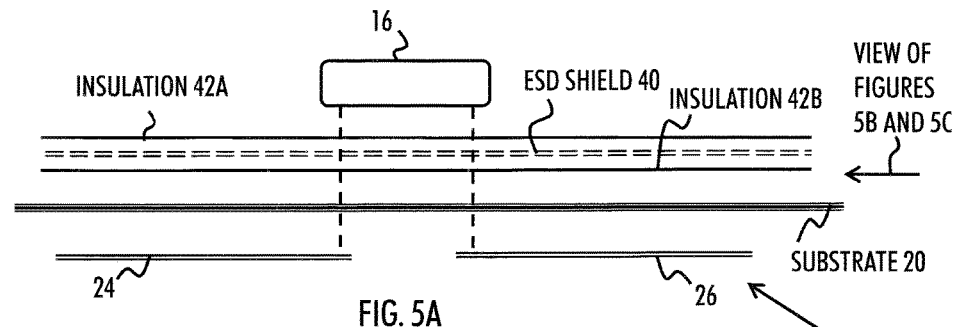
FIG. 5A shows an insulation applied to the ESD shield according to an embodiment.

In an embodiment, as shown in FIG. 5A, the flexible ESD shield 40 is electrically insulated from the textile substrate 20 and from the at least two electrodes 24, 26. This may be beneficial, for example, when the textile substrate 20 absorbs moisture during the exercise which may lead the textile substrate to become at least somewhat electrically conducting. Such electrical conduction of the textile substrate 20 may cause any non-insulated ESD shield to be in electrical contact with the skin 32 via the conductive substrate 20 in an uncontrollable manner (depending on the location of the ESD shield 40). This may cause the signal-to-noise ratio (SNR) of the ECG signal to become weaker, thus leading to poorer ECG measurement accuracy. However owing to the electrical insulation applied to the ESD shield 40 according to this embodiment, the ESD shield 40 does not become uncontrollably contacted with the skin 32, for example. Further, it may be important that the ESD shield 40 is not in electrical contact with the electrodes 24, 26. Thus, depending on the location of the ESD shield 40, an electrical insulation between the ESD shield 40 and the electrode 24, 26 (electrode layer 30) may be provided.

In an embodiment, the ESD shield 40 comprises at least one layer 42A, 42B made of an electrically non-conducting material which provides for the electrical insulation. The insulation may be obtained with a plastic or thermoplastic tape glued onto the ESD shield 40, for example. In an embodiment, in case the ESD shield 40 is on top of the flexible substrate 20, as shown in FIG. 5A, the insulation layer 42A may be omitted. However, in case the ESD shield 40 is between the flexible substrate 20 and the electrode layer 30, as is the case in FIG. 4B, there may be need to apply both of the insulation layers 42A and 42B on both sides of the ESD shield 40 in order to obtain electric insulation to the electrodes 24, 26 and also to the flexible substrate 20. The insulation layers 42A, 42B may be wider and longer than the ESD shield 40 in order to provide for efficient insulation.

In an embodiment, the ESD shield 40 is formed into a sock-like structure comprising both of the insulation layers 42A, 42B, which provides for the electric insulation from the ESD shield structure 40 to the flexible substrate 20 to the electrodes 24, 26. In the sock-like structure, the insulation layers 42A, 42B may be attached to each other at least at one end, although not shown in the Figures. In an embodiment, the insulation layers 42A, 42B are attached to each other at both ends. In an embodiment, as shown in FIG. 5B which shows a horizontal view along the skin 32 of the person 60, the insulation layers 42A, 42B are attached to each other longitudinally at sides to form the sock-like structure.

In FIGS. 4A to 5C, dashed lines show how the electrical connection between the electrodes 24, 26 and the electronics module 16 is provided. The electrical connection, such as an electrically conducting wire, may penetrate the flexible textile substrate 20, the ESD shield 40 and/or the insulation layer(s) 42A, 42B. The penetration may be provided with through-holes in the flexible textile substrate 20, in the ESD shield 40 and/or in the insulation layer(s) 42A, 42B. The through-holes may be electrically insulated from the corresponding layer to which they are formed, e.g. from the flexible textile substrate 20, the ESD shield 40 and/or the insulation layer(s) 42A, 42B. This may be beneficial so as conduct the measured ECG signals only to the electronics module 16 and not to the layers of the heart activity sensor structure 100.

Figure 5B:
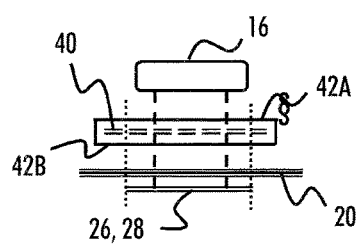
FIGS. 5B and 5C illustrate electrical connection between electrodes and an electronics module according to some embodiments
Figure 5C:
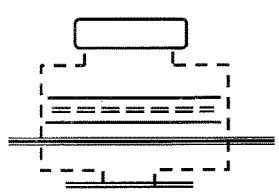

For example, looking horizontally along the skin 32 of the person 60, FIG. 5B shows how the electrical connection penetrates the flexible textile substrate 20, the ESD shield 40 and the insulation layer(s) 42A, 42B. However, FIG. 5C shows how the electrical connection, such as a wire, may be arranged to circulate the ESD shield 40 and the insulation layer(s) 42A, 42B from the sides (an upper side and a lower side when the heart activity sensor structure 100 is worn on the chest of the exerciser 60). This may be beneficial to avoid implementing through-holes in the ESD shield 40 and in the insulation layer(s) 42A, 42B. It should be noted that the electrical connection, such as wires, may travel at least partly inside the flexible substrate 20 to which the electrodes 24, 26 may be mounted.

Figure 6A:
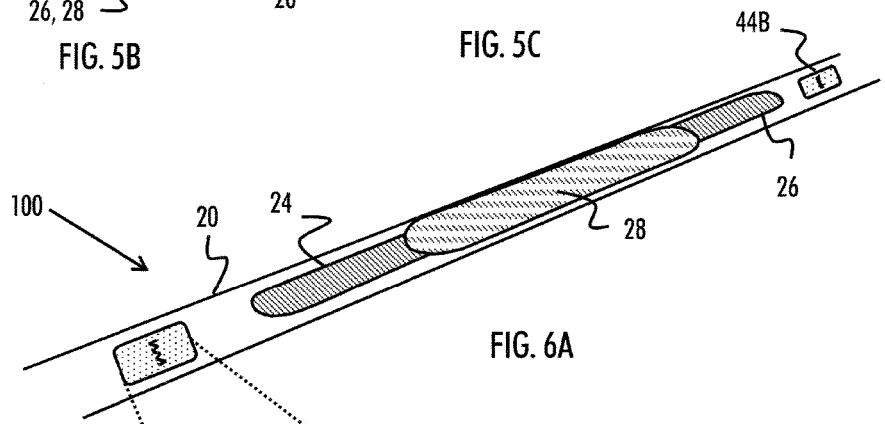
FIGS. 6A and 6B depict grounding elements according to an embodiment.
Figure 6B:
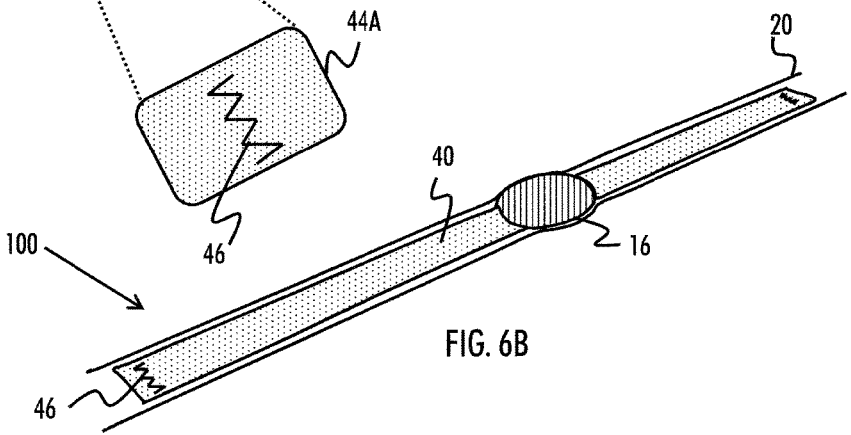

In an embodiment, the heart activity sensor structure 100 further comprises, as shown in FIGS. 6A and 6B, at least one grounding element 44A, 44B coupled to the ESD shield 40 and configured to contact the skin 32 of the exerciser 60 during use. This at least one grounding element 44A, 44B provides for grounding of the ESD shield 40 to the skin 32 and therefore acts as a gateway for the static electricity to pass to the skin 32 which may be seen as an electrical ground. FIG. 6A shows the heart activity sensor structure 100 from the side which is against the skin 32 of the exerciser 60 during use, whereas FIG. 6B shows an opposite (top) view of the heart activity sensor structure 100. In these Figures, it is assumed that the ESD shield 40 is placed on top of the flexible textile substrate 20. The grounding element(s) 44A, 44B may be made of any conducting material.

In an embodiment, at least one location in which the at least one grounding element 44A, 44B contacts the skin is at the at least one end of the flexible textile substrate 20. However, in order to provide more efficient grounding, in an embodiment, there are two grounding elements 44A, 44B, one at each end of the flexible textile substrate 20. An end of the flexible textile substrate 20 may be defined as an area between the longitudinal end of the flexible textile substrate 20 and the electrode 24 or 26 on the respective longitudinal side of the flexible textile substrate. In case there exists at least one insulation layer 42A, 42B, there may be a through-hole in the respective insulation layer(s) 42A, 42B, through which the ESD shield 40 may be connected to the at least one grounding element 44A, 44B.

In an embodiment, the heart activity sensor structure 100 further comprises a conducting string structure 46 for coupling the at least one grounding element 44A, 44B and the ESD shield 40, wherein the conducting string structure 46 penetrates the textile substrate 20. As shown in FIGS. 6A and 6B, the ESD shield 40 may be on top of the textile substrate 20 whereas the electrode layer 30 (comprising electrodes 24, 26) is on the opposite side of the textile substrate 20. In such case, the conducting string structure 46 may provide a reliable and cost-efficient manner of electrically coupling the ESD shield 40 to the grounding element(s) 44A, 44B. The string structure 46 may be, for example, a metal string attached (e.g. knitted, woven) to the ESD shield 40 and to the respective grounding element 44A, 44B. For example, from the point of view of manufacturing the heart activity sensor structure 100, the string structure 46 may be easily added (e.g. knitted, woven) to the heart activity sensor structure 100 without having to make any special through-holes or a like in the flexible textile substrate 20. Similarly, the string structure 46 may penetrate the insulating layer 42B, if such is used.

In the case both the electrode layer 30 and the ESD shield 40 are on the same side of the flexible textile substrate 20 (not shown in FIGS. 6A, 6B), the grounding element(s) 44A, 44B may be directly attached to the ESD shield 40. In an embodiment referring to such order of the layers, there may be hole(s) in the insulation layer 42B which allow the ESD shield 40 to contact the skin 32 during use. In this embodiment, the portion(s) of the ESD shield 40 touching the skin 32 may be seen as the grounding element(s) 44A, 44B. In yet one embodiment referring to such order of the layers, the grounding element(s) 44A, 44B may be also in this case connected to the ESD shield 40 via the conducting string structure 46 penetrating the insulation layer 44B, if such exists. It should be noted that the intermediate insulation layer 22 of FIG. 3 may provide for the insulation between the electrodes 24, 26 and the ESD shield 40, instead of the insulation layer 44B. In such case, if the ESD shield is longer than the intermediate insulation layer 22, the portion(s) of the ESD shield 40 extending further than the intermediate insulation layer 22 may be seen as the grounding element(s) 44A, 44B contacting the skin 32 of the exerciser 60.

In an embodiment, the heart activity sensor structure 100 comprises an electronics module 16 configured at least to transmit information related to the heart activity to the training computer 16, as indicated with reference to FIGS. 1A and 1B. The electronics module 16 may further comprise also other functional entities than the transmitter, as described earlier.

Figure 7A:
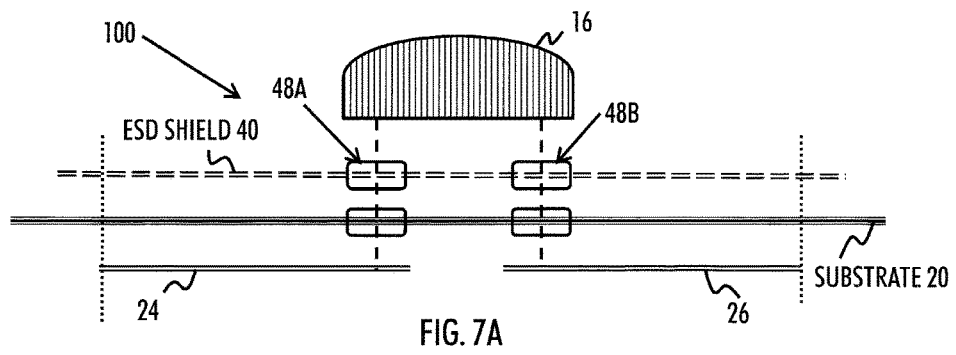
FIGS. 7A, 7B, and 7C illustrate mounting of the electronics module according to some embodiments.

In an embodiment, as shown in FIG. 7A, the electronics module 16 is detachably coupled to the at least two electrodes 24, 26. In this case, there may be the press studs 12, 14 or other electromechanical connectors which provide for the attaching and detaching of the electronics module 16 to/from the substrate 20. Further, in this case the ESD shield 40 may comprise at least one through-hole 48A, 48B in order to allow the electrical coupling between the at least two electrodes 24, 26 and the electronics module 16 to pass the ESD shield 40. As said, also the substrate 20 may comprise through-holes for allowing the electrical connection to pass. The through-holes may be electrically insulated from the layer to which they are formed.

Figure 7B:
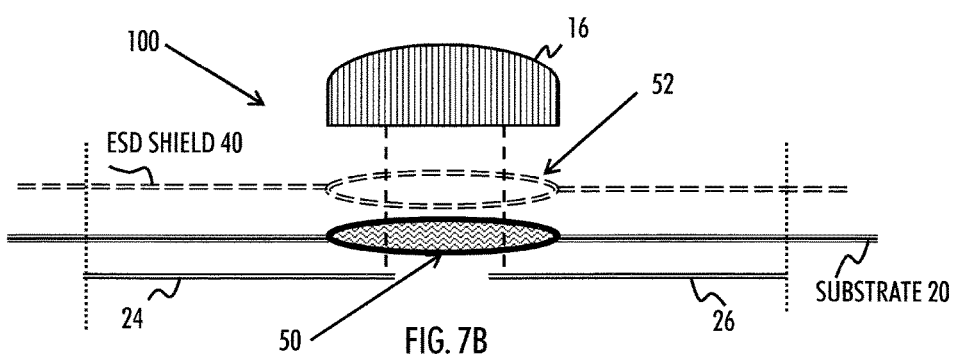
Figure 7C:
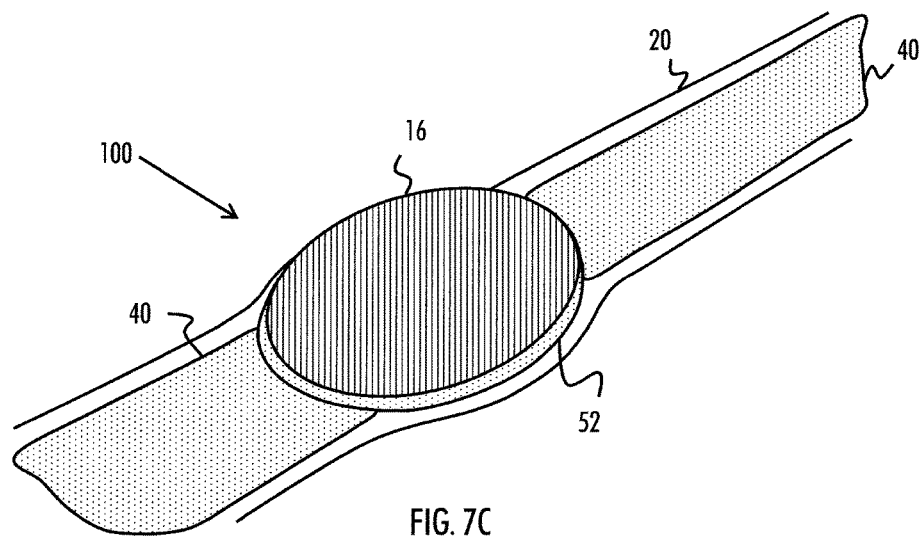

However, in an embodiment, the electronics module 16 is integrated (non-detachably) as part of the heart activity sensor structure 100. In this case, the electronics module 16 is, as shown in FIGS. 7B and 7C, mounted integrally to a base 50 of the substrate 20. In an embodiment, the base 50 may be an engraving in the substrate 20, wherein the dimensions of the engraving may be appropriate to fit the electronics module 16. In another embodiment, the base 50 may be a location on the surface of the substrate 20 to which the electronics module 16 is mounted to. The attachment between the electronics module 16 and the base 50 may be obtained with glue, for example. The base 50 and the electronics module 16 may comprise electrical connecting elements which provide for electrical connection between the electronics module 16 and the electrodes 24, 26.

In an embodiment, the heart activity sensor structure 100 comprises a first part of the ESD 40 on one side of the electronics module 16 and a second part of the ESD 40 on the other side of the electronics module 16. The first and second parts may be electrically separated from each other. However, in an embodiment, the electronics module 16 comprises a conducting structure configured to electrically connect the first part and the second part with each other. Such conducting structure may, e.g. in a casing that covers the electronics module 16.

Figure 8:
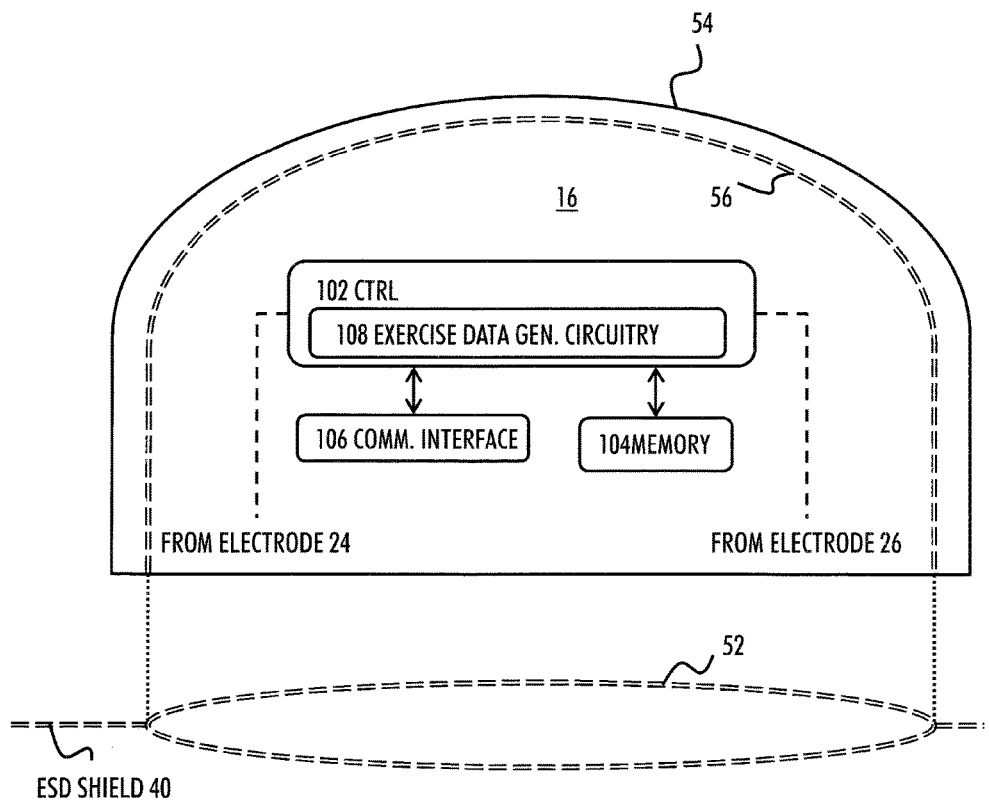
FIG. 8 shows the electronic module according to an embodiment.

In an embodiment, the heart activity sensor structure 100 and, more particularly, the base 50 comprises electrically conducting periphery element 52 coupled to the ESD shield 40, as shown in FIGS. 7B, 7C and 8. The periphery element 52 may be in the form of a ring, an ellipse or a rectangular, to mention only a few possibly non-limiting options. The shape of the periphery element 52 may depend on the shape of the base 50, for example. Thus, the ESD shield 40 may advantageously be a continuous element in front of the electrodes 24, 26. As shown, the periphery element 52 may be electrically connected to the ESD shield 40, thus forming part of the ESD shield 40.

In an embodiment, as shown in FIG. 8, the electronics module 16 comprises a casing covering the electronics module 16. The casing may comprise an electrically non-conductive outer surface 54 and electrically conductive inner film 56. The electrically non-conductive outer surface 54, which may be of plastic, may be beneficial so as no electric shocks are passed to the exerciser 60 touching the electronics module 16.

There may be static electricity generated in the electronics module 16 due to the movement of the shirt 34 against the module 16, for example. Thus, in such case, the electrically conductive inner film 56 may be of importance in protecting the electronic components of the electronic module 16 from the ESD of the static electricity. Accordingly, in an embodiment, the electrically conductive inner film 56 may be electrically coupled to the ESD shield 40. This may take place either directly or via the periphery element 52 of the base 50. In the latter case, the electrically conducting periphery element 52 may be coupled to the electrically conductive inner film 56 of the electronics module 16, as shown in FIG. 8. As a result, the inner film 56 may form part of the (continuous) ESD shield 40. This may provide protection for the electronic components inside the electronics module 16 and also provide more efficient shielding of the electrodes 24, 26.

In an embodiment, the surface of the base 50 is electrically conductive and acts as part of the ESD shield 40. There may be electric insulations applied in required portions of the base in order to ensure that, for example, the electrical connection between the module 16 and the electrodes 24, 26 is not affected by the ESD shield 40.

In an embodiment, the surface of the base 50 is electrically conductive and the electronics module 16 comprises the electrically conductive inner film 56, and these electrically conductive portions are coupled to each other. This embodiment may create a Faraday's cage or shield for the electronics module 16, thus protecting it from static electricity efficiently.

It should be noted that FIGS. 4A to 5C, 7A, 7B, and 8 are explosion Figures. Thus, it is clear that although the layers/components in the Figures are drawn separated from each other, the layers/components may be attached layer wise on top of each other to form the heart activity sensor structure 100. In an embodiment, the ESD shield 40 is at least partially inside the flexible textile substrate 20.

As shown in FIG. 8, the electronics module 16 may comprise a control circuitry (CTRL) 102, such as at least one processor, and at least one memory 104 including a computer program code, wherein the at least one memory 104 and the computer program code, are configured, with the at least one processor 104, to cause the electronics module 16 to carry out a specific task with respect to the detected ECG signal, for example. The memory 104 may be implemented using any suitable data storage technology, such as semiconductor based memory devices, flash memory, magnetic memory devices and systems, optical memory devices and systems, fixed memory and removable memory.

The control circuitry 102 may comprise an exercise data generation circuitry 108 for generating the exercise data related to the detected ECG signals. The generated data may represent, for example, heart rate or heart rate variation. The apparatus may further comprise communication interface 106 comprising hardware and/or software for realizing communication connectivity according to one or more communication protocols, such as Bluetooth, Bluetooth Smart, wireless local area network (WLAN, WiFi), infrared (IR), wireless communication utilizing electric and/or magnetic fields, ANT, ANT+, or WIND. The communication connection may be applied for transmitting exercise data to the training computer 17 or to receive data from the training computer 17, for example.

Figure 9:
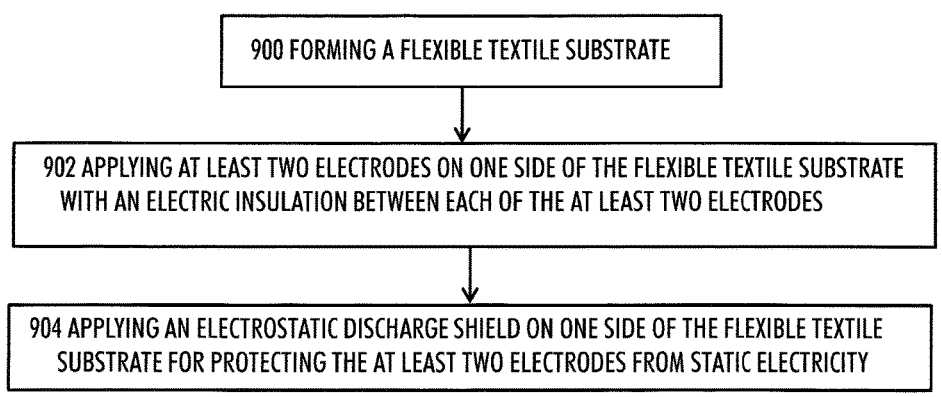
FIG. 9 illustrates a method according to an embodiment.

There is also provided a method, as shown in FIG. 9, comprising, in step 900, forming a flexible textile substrate. In step 902, the method comprises applying at least two electrodes 24, 26 on one side of the flexible textile substrate 20 with an electric insulation between each of the at least two electrodes 24, 26, wherein the at least two electrodes 24, 26 are configured to be placed against a skin 32 of an exerciser 60 in order to measure biosignals related to heart activity. In step 904, the method comprises applying an electrostatic discharge shield 40 on one side of the flexible textile substrate 20 for protecting the at least two electrodes 24, 26 from static electricity.

As used in this application, the term 'circuitry' refers to all of the following: (a) hardware-only circuit implementations, such as implementations in only analog and/or digital circuitry, and (b) combinations of circuits and software (and/or firmware), such as (as applicable): (i) a combination of processor(s) or (ii) portions of processor(s)/software including digital signal processor(s), software, and memory(ies) that work together to cause an apparatus to perform various functions, and (c) circuits, such as a microprocessor(s) or a portion of a microprocessor(s), that require software or firmware for operation, even if the software or firmware is not physically present. This definition of 'circuitry' applies to all uses of this term in this application. As a further example, as used in this application, the term 'circuitry' would also cover an implementation of merely a processor (or multiple processors) or a portion of a processor and its (or their) accompanying software and/or firmware. The term 'circuitry' would also cover, for example and if applicable to the particular element, a baseband integrated circuit or applications processor integrated circuit for a mobile phone or a similar integrated circuit in a server, a cellular network device, or another network device.

Some of the functionalities performed by the electronics module 16 embodiments as described may also be carried out in the form of a computer process defined by a computer program. The computer program may be in source code form, object code form, or in some intermediate form, and it may be stored in some sort of carrier, which may be any entity or device capable of carrying the program. For example, the computer program may be stored on a computer program distribution medium readable by a computer or a processor. The computer program medium may be, for example but not limited to, a record medium, computer memory, read-only memory, electrical carrier signal, telecommunications signal, and software distribution package, for example. Coding of software for carrying out the embodiments as shown and described is well within the scope of a person of ordinary skill in the art.

Even though the invention has been described above with reference to an example according to the accompanying drawings, it is clear that the invention is not restricted thereto but can be modified in several ways within the scope of the appended claims. Therefore, all words and expressions should be interpreted broadly and they are intended to illustrate, not to restrict, the embodiment. It will be obvious to a person skilled in the art that, as technology advances, the inventive concept can be implemented in various ways. Further, it is clear to a person skilled in the art that the described embodiments may, but are not required to, be combined with other embodiments in various ways.

What is claimed is:

1. A heart activity sensor structure, comprising:
   a flexible textile substrate;
   at least two electrodes with an electric insulation between each of the at least two electrodes, wherein the at least two electrodes are applied on one side of the flexible textile substrate and configured to be placed against a skin of an exerciser in order to measure biosignals related to heart activity;
   an electrostatic discharge shield applied on one side of the flexible textile substrate for protecting the at least two electrodes from static electricity, the electrostatic discharge shield comprising conductive material, wherein the electrostatic discharge shield covers at least an area of the heart activity sensor structure in which the at least two electrodes and all regions between the at least two electrodes are disposed; and
   an electronics module integrated as part of the heart activity sensor structure, coupled to the at least two electrodes and configured at least to transmit information related to the heart activity to a training computer, the electronics module comprising a casing covering the electronics module, the casing comprising an electrically non-conducting outer surface and electrically conducting inner film, the electrically conducting inner film being electrically coupled to the electrostatic discharge shield, wherein the flexible textile substrate comprises a base for integrally mounting the electronics module, wherein the base comprises an electrically conducting periphery element coupled to the electrostatic discharge shield, wherein the electronics module is configured at least to transmit information related to the heart activity to a training computer, wherein a first part of the electrostatic discharge shield is on one side of the electronics module and a second part of the electrostatic discharge shield is on an other side of the electronics module, wherein the electronics module comprises a casing having a conducting structure configured to cover the electronics module and electrically connect the first part of the electrostatic discharge shield to the second part of the electrostatic discharge shield.

2. The heart activity sensor structure of claim 1, comprising at least the following plurality of layers:
   a first layer comprising the at least two electrodes and configured to be placed against the skin of the exerciser;
   a second layer arranged on top of the first layer and comprising the flexible textile substrate; and
   a third layer arranged at least partially on top of the second layer and comprising the electrostatic discharge shield.

3. The heart activity sensor structure of claim 1, comprising at least the following plurality of layers:
   a first layer comprising the at least two electrodes and configured to be placed against the skin of the exerciser;
   a third layer arranged on top of the first layer and comprising the electrostatic discharge shield; and
   a second layer arranged on top of the third layer and comprising the flexible textile substrate.

4. The heart activity sensor structure of claim 1, wherein the electrostatic discharge shield covers at least the area of the heart activity sensor structure in which the at least two electrodes are located.

5. The heart activity sensor structure of claim 1, wherein the electrostatic discharge shield is electrically insulated from the flexible textile substrate and from the at least two electrodes.

6. The heart activity sensor structure of claim 5, wherein the electrostatic discharge shield comprises at least one layer made of an electrically non-conducting material which provides for the electrical insulation.

7. The heart activity sensor structure of claim 1, wherein at least one location in which the at least one grounding element is configured to contact the skin is at the at least one end of the flexible textile substrate.

8. The heart activity sensor structure of claim 1, further comprising:
   a conducting string structure for coupling at least one grounding element and the electrostatic discharge shield, wherein the conducting string structure penetrates the flexible textile substrate.

9. The heart activity sensor structure of claim 1, further comprising:
   an electronics module detachably coupled to the at least two electrodes and configured at least to transmit information related to the heart activity to a training computer, wherein the electrostatic discharge shield comprises at least one through-hole in order to enable the coupling between the at least two electrodes and the electronics module.

10. A method for manufacturing a heart activity sensor structure, comprising:
    forming a flexible textile substrate;
    applying at least two electrodes on one side of the flexible textile substrate with an electric insulation between each of the at least two electrodes, wherein the at least two electrodes are configured to be placed against a skin of an exerciser in order to measure biosignals related to heart activity;
    applying an electrostatic discharge shield on one side of the flexible textile substrate for protecting the at least two electrodes from static electricity, the electrostatic discharge shield comprising conductive material, wherein the electrostatic discharge shield covers at least an area of the heart activity sensor structure in which the at least two electrodes and all regions between the at least two electrodes are disposed; and
    coupling first and second grounding elements to the electrostatic discharge shield and arranging the first and second grounding elements such that the at least two electrodes are situated between the first and second grounding elements, the first and second grounding elements configured to be placed against the skin of the exerciser and to conduct, together with the electrostatic discharge shield, electrostatic discharges away from the at least two electrodes, wherein the flexible textile substrate comprises a base for integrally mounting an electronics module, wherein the base comprises an electrically conducting periphery element coupled to the electrostatic discharge shield, wherein the electronics module is configured at least to transmit information related to the heart activity to a training computer, wherein a first part of the electrostatic discharge shield is on the other side of the electronics module and a second part of the electrostatic discharge shield is on an other side of the electronics module, wherein the electronics module comprises a casing having a conducting structure configured to cover the electronics module and electrically connect the first part of the electrostatic discharge shield to the second part of the electrostatic discharge shield.

11. The method of claim 10, wherein the flexible textile substrate, the at least two electrodes, the electrostatic discharge shield are each comprised in a dedicated layer, and the method comprises attaching the layers on top of each other.

* * * * *